United States Patent [19]
Stewart et al.

[11] 3,981,991
[45] Sept. 21, 1976

[54] STABILIZATION OF INTERFERON
[75] Inventors: William Edgar Stewart, Herent; Pierre Marie Hendrik Frans de Somer, Leuven, both of Belgium
[73] Assignee: Stichting REGA V.Z.W., Leuven, Belgium
[22] Filed: Apr. 3, 1975
[21] Appl. No.: 564,723

[30] Foreign Application Priority Data
Apr. 3, 1974  Netherlands ...................... 7404589

[52] U.S. Cl. ................................................. 424/85
[51] Int. Cl.² ......................................... A61K 45/02
[58] Field of Search ....................................... 424/85

[56] References Cited
OTHER PUBLICATIONS
Stewart et al., Nature, vol. 249, May 31, 1974, pp. 460–461.

Primary Examiner—Shep K. Rose
Attorney, Agent, or Firm—Stewart and Kolasch, Ltd.

[57] ABSTRACT
An aqueous interferon solution is stabilized by treatment with a combination of (a) an agent for disrupting non-covalent bonds, (b) an agent for reducing disulfide bridges, and (c) an anionic or cationic surface-active agent.

7 Claims, No Drawings

STABILIZATION OF INTERFERON

This invention relates to the stabilization of interferon.

Interferon is the name given to a cellular antivirus material which may be recovered from living cells and from extracellular fluids. Its productions in the cells may be stimulated by several agents, including in the first place viruses and further a variety or other agents ranging from bacteria to high-molecular polymers. The interferon may be recovered from the cells or extracellular fluids in different degrees of purity and appears to be capable of protecting animal tissues and cells against viral attack. In general, the anti-virus activity of interferon is non-specific in its power to give protection against other viruses in addition to those which have been used for stimulating the cells although differences in sensitivity to interferon have been observed between different viruses. In most cases, interferon is found to give a better protection to tissues and cells of the kind from which it has been produced than to other tissues and cells.

General surveys of the present knowledge about interferon may be found in the books: "Interferon" by J. Vilcek, Springer-Verlag, Vienna-New York, 1969, and "Selective Inhibitors of Viral Functions" by W. A. Carter (ed), CRC-Press, Cleveland, 1973, which are incorporated herein by way of reference.

Although much work has been done relating to the physical and chemical characterisation of interferon, it has not yet been possible to determine its chemical structure with certainty. It seems evident that interferon is of proteinic nature but most of the details thereof are uncertain. The determination of this chemical structure has been hampered to a great extent by the fact that there seem to be several molecular species of interferon, such species having different molecular weights and different characteristics and their formation being dependent from several factors such as the nature of the cells used for interferon production (e.g. cells from different animal species such as mouse, rabbit, chicken or man, or cells derived from different tissues of a single animal species), the nature of the agent used for production stimulation (e.g. different viruses), the actual production method and the actual method of recovering interferon from cells or fluids.

Further, the production, purification and clinical evaluation of interferon has been hampered up till now by several factors, the most important thereof being the reputed instability of interferon. Although it has been reported that some types of interferon such as human leukocyte interferon and rabbit interferon, are more or less stable against inactivation, other types of interferon are readily inactivated by several circumstances such as prolonged storage, undesired pH values, elevated temperatures and chemical and mechanical manipulations such as shaking, repeated freezing and thawing cycles, frothing during filtration, and the like. Still other types of interferon, such as human fibrolast interferon, have such instability that their activity levels are not reliable. Further, even the relatively most stable types of interferon appear to become labile as soon as a high degree of purity has been reached. To overcome these problems it has been proposed to add extraneous proteins to protect the interferon during its purification but this protein addition has many disadvantages because most types of interferon will resist protection and the object of purification is counteracted thereby. Thus, there is a constant need for a method of stabilisation of interferon in an efficient way and especially a need for a method of stabilizing all types of interferon that are less stable to inactivation, either by their nature or as a result of continued purification.

The invention has for its object to satisfy this need and to provide a method of stabilising interferon which does not have the aforesaid disadvantages. Moreover, the invention has for its object to provide a stabilised interferon suitable for further purification and clinical evaluation without substantial loss of its activity.

In accordance with the invention, it has now been found that interferon may be stabilized by treatment with a combination of three reagents, viz. (a) an agent for disrupting non-covalent bonds, such as urea or guanidine-hydrochloride, (b) an agent for reducing disulfide bonds, such as mercaptoethanol, and (c) an anionic or cationic surface-active agent such as sodium dodecyl sulfate or dodecyl amine. When treated with these reagents, the interferon will substantially maintain its initial activity and will be stable against inactivation under the influence of the aforesaid circumstances and manipulations.

Thanks to this unexpected discovery, it is possible now to prepare a stable interferon product which is suitable for further purification and clinical evaluation. Moreover, it is possible now to start the production of interferon on a larger scale.

The mechanism of stabilisation brought about by the invention is not yet quite clear. Suppose, however, that the interferon molecule comprises a polypeptide chain having covalent and non-covalent bonds and further having one or more disulfide bridges, then the native form or conformation of the molecule is presumably converted by the agent for disrupting non-covalent bonds and the agent for reduction of disulfide bridges to another conformation showing a so-called "linear random coil" and having free sulfhydryl groups. Thereafter, the surface-active agent may bind to the charged groups on the polypeptide molecule and shield the liberated sulfhydryl groups and thereby protect these groups against re-oxidation accompanied by intramolecular or intermolecular re-formation of disulfide bridges. Although these reactions bring about a denaturation of the interferon molecule, they nevertheless have a protection action and thus, it is possible to speak of a protective denaturation. If desired, the resulting product may be freed of the disrupting and reduction agents and freed from the excess of surface-active agent by means of dialysis. When the product is incubated later on with a protein-containing medium, such as a medium comprising living cells, the product will spontaneously develop an active conformation which substantially has the initial activity of native interferon. The whole process can be described as a stabilisation of interferon by protective denaturation.

It will be evident of course, that the invention is not limited by this theoretical explanation. Instead thereof, the invention embraces all features and materials falling within the scope of the appended claims.

In carrying out the method of the present invention, the starting material may be any type of native or purified interferon in a state resulting from production and/or purification, provided that it has lost substantially nothing of its initial activity. The source of the interferon is not especially critical although there is a preference for those types of interferon which are relatively instable by nature or instable as a result of purification such as mouse interferon and human fibroblust interferon. In most cases, this interferon is available in the form of an aqueous solution having an activity between about $10^3$ and $10^8$ interferon units per milligram of protein (or about $10^1$ to about $10^6$ interferon units per milliliter of solution) and this solution may be used as such for the method of the invention.

According to the invention, this interferon is treated with a combination of three reagents, viz. an agent for disrupting non-covalent bonds, an agent for reducing disulfide bridges and an anionic or cationic surface active agent.

The agent for disrupting non-covalent bonds may be any suitable agent of this type. Typical examples are urea and guanidine-hydrochloride whereby urea is preferred.

The amount of such agent used in the method of the invention should be sufficient to bring about unfolding of the polypeptide chain of the interferon molecule in order to result in a "linear random coil". In general, the amount of urea as used is such that the resulting solution comprises from 0.1 to 10 M of urea and preferably, the concentration is 5 M of urea. Lower concentrations than 0.1 M will be without effect and higher concentrations than 10 M are useless because the saturation point has then been reached.

The agent for reducing disulfide bridges may be any conventional agent of this type. A typical example is ethanethiol or mercaptoethanol. The amount thereof as used in the method of the invention should be sufficient to reduce all the disulfide bridges in the interferon molecule as far as they are present therein. In most cases, the amount of mercaptoethanol is such that the resulting solution comprises at least $10^{-2}M$ of mercaptoethanol. Lower amounts than $10^{-2}M$ will have little or no effect. An upper limit can hardly be given because higher amounts are not disadvantageous. It is preferred to use concentrations of about $1.4 \times 10^{-2}M$ to $1.4 \times 10^{-1}M$ of mercaptoethanol in the solution.

The anionic or cationic surface-active agent may be any conventional agent of this type. An alkyl sulfate having 8 to 22 carbon atoms in its alkyl group, such as sodium dodecylsulfate or sodium decylsulfate, will in most cases be sufficient as an anionic surface-active agent, but a corresponding alkyl sulfonate such as sodium dodecylsulfonate may also have the desired effect. The cationic agent will be, in general, an alkylamine having 8 to 22 carbon atoms in its alkyl group, such as dodecylamine or decylamine. The amount of this agent as used should be sufficient to bind to the protein and to shield the sulfhydryl groups of the interferon molecule liberated by the aforesaid reduction agent. In order to be sure of the desired effect, a 1-fold to 5-fold excess of surface-active agent calculated on the total amount of protein in solution will be used in most cases. If the starting material is an interferon solution comprising about $10^4$ interferon units per millimeter, this will mean that the solution should comprise at least $1 \times 10^{-3}$ and at most $1 \times 10^{-1}M$ of surface-active agent. An amount of $3.5 \times 10^{-3}M$ to $3.5 \times 10^{-2}M$ of sodium dodecylsulfate is preferred in that case.

The addition sequence of the three reagents is not critical although it is preferred to add the surface-active agent simultaneously with or prior to the other two agents in order to be sure that this surface-active agent is able to react with charged groups on the peptide backbone to shield the sulfhydryl groups as soon as they have been liberated by the reduction agent. It is preferred to add all three agents substantially at the same time or one shortly after the other.

The reactions of said three agents with the interferon may proceed smoothly at room temperature or in general at a temperature from 15°C to 30°C. Thus, no special measures for accelerating these reactions will be needed. After reaction, the excess of surface-active agent and the whole amount of the other two reagents may be removed by dialysis, although this is not absolutely necessary.

The treatment with said three reagents will result in a complete stabilisation of interferon against inactivation-provoking circumstances and manipulations such as prolonged storage, excessive heating and the like. After treatment with urea, mercaptoethanol and sodium dodecylsulfate, both human interferon and mouse interferon appear to be completely stable against heating at 56°C and 100°C. A prolonged boiling treatment in the presence of the three reagents will result in a slight loss of activity but if the urea is removed by dialysis prior to boiling, then the interferon remains stable even at prolonged boiling.

It must be observed that the same effect cannot be obtained with only one or two of the aforesaid three reagents. Thus, urea and mercaptoethanol, when used alone or together, will have no stabilising effect but rather an instability-promoting effect on interferon. Presumably, the interferon is still converted to a "linear random coil" having free sulfhydryl groups but the molecule is not protected against oxidation in this way and so it is nearly completely inactivated during a boiling treatment.

In the case that a surface-active agent is added alone to interferon, then the activity thereof will decrease by 60 to 90% during boiling treatment of the product. The remaining activity will be maintained at the same level as long as the surface-active agent is present but a complete stabilisation of the interferon always requires a combination of the aforesaid three reagents.

The method of interferon stabilisation as disclosed in this specification offers a possibility for stabilising interferon in several states of recovery and purification and also offers a possibility for prolonged storage of interferon. A relatively pure stabilised interferon having a specific activity of about $10^8$ units per milligram of protein may thus be administered clinically in stabilised form. In view of the fact that proteins in general only bind 1.44 grams of sodium dodecylsulfate per gram of protein, a dosage containing millions of units of interferon will only comprise a few micrograms of sodium dodecylsulfate and so, no risk for complications in clinical administration may be expected.

The following examples are meant to illustrate some details and not to restrict the invention.

EXAMPLE 1

The starting material was a solution of mouse interferon derived from cells of the $L_{929}$-type stimulated by Newcastle disease virus. This solution was acidified to a pH of 2, whereupon extraneous proteins were precipitated by addition of ammonium sulfate until a saturation degree of 20% at 20°C was reached. The clarified solution was adjusted to a pH of 7.2 by dialysis against a 0.01 M TRIS-HCl buffer. The resulting purified solution had an activity of $10^4$ interferon units per millimeter (determined by biological assay).

To an aliquot portion of this purified interference solution was added an aqueous solution of sodium dodecyl sulfate (SDS) followed immediately by solid urea and liquid mercaptoethanol. The added amounts were such that the resulting solution comprised 5M of urea, $1.4 \times 10^{-2}$M of mercaptoethanol and $3.5 \times 10^{-3}$M of SDS. The resulting solution was heated at 56°C during 60 minutes but no change in appearance could be observed. A biological assay revealed that the interference activity had been maintained on the same level. Similar results were obtained after 2½ minutes boiling at 100°C and after 30 cycles of freezing (in a mixture of dry ice and acetone) and thawing (at 37°C). Thus, the treated interferon solution appeared to be completely stabilised against inactivity-provoking circumstances and manipulations. For control, another aliquot portion of the purified starting solution was subjected to the same tests without addition of the aforesaid reagents. The activity of the solution decreased to about 10% of its initial value after heating at 56°C during 60 minutes and also decreased to about 10% of its initial value after 30 freeze-thaw cycles. In the boiling test, it appeared that the interferon activity had already decreased to a value below $10^1$ interferon units per milliliter after 1 minute of boiling at 100°C. A precipitate occurred after 2 minutes of boiling. This untreated interferon solution was therefore very labile to inactivity-provoking circumstances and manipulations.

EXAMPLE 2

To an aliquot portion of the same purified mouse interferon solution as used in Example 1, was added a solution of SDS followed by solid urea and liquid mercapto-ethanol. These agents were added in such amounts that the resulting solution comprised 5M of urea, $1.4 \times 10^{-1}$M of mercaptoethanol and $3.5 \times 10^{-2}$M of SDS. The resulting solution was subjected to the same tests as in Example 1 and the results thereof were similar. Thus, the treated interferon solution was completely stabilised against inactivity-provoking circumstances and manipulations.

For control, another aliquot portion of the purified starting solution was subjected to the same tests without addition of the aforesaid three reagents. Similarly to the control tests in Example 1, this solution lost most of its activity by heating at 56°C and by 1 minute of boiling at 100°C. The untreated interferon solution was, therefore, very labile to inactivity-provoking circumstances and manipulations.

EXAMPLE 3

The starting material was a solution of human interferon, derived from human diploid fibroblast cells stimulated with synthetic double-stranded polyribonucleic acid, polyriboinosic acid and polyribocytidylic acid. The pH of this material was adjusted to a value of 7.2 by means of dialysis against a 0.01 M TRIS-HCl buffer. The resulting solution had an activity of about $10^4$ interferon units per milliliter (determined by biological assay).

To an aliquot portion of this interferon solution were added the following substances: first an aqueous solution of sodium dodecyl sulfate, then solid urea and liquid mercaptoethanol. The added amounts were such that the resulting solution comprised 5 M of urea, $1.4 \times 10^{-2}$M of mercaptoethanol and $3.5 \times 10^{-3}$M of SDS. The resulting solution was subjected to the same tests as in Example 1 and similar results were obtained thereby. Thus, the treated interferon solution was completely stabilised against inactivity-provoking circumstances and manipulations.

For control, another aliquot portion of the purified interferon solution was subjected to the same tests without the addition of reagents. The results were similar to the control tests in Example 1, i.e. only 10% of activity left after heating at 56°C and 30 freeze-thaw cycles, and moreover, less than $10^1$ interferon units per milliliter left after 1 minute of boiling at 100°C. This untreated solution was therefore very labile to inactivity-provoking circumstances and manipulations.

EXAMPLE 4

To an aliquot portion of the same purified human interferon solution as used in Example 3, was added a solution of SDS, followed by solid urea and liquid mercaptoethanol, in such amounts that the resulting solution comprised 5M of urea, $1.4 \times 10^{-1}$M of mercaptoethanol and $3.5 \times 10^{-2}$M SDS. The resulting solution was subjected to the same tests as in Example 1 and the results thereof were similar Thus the treated interferon solution was again completely stabilised against inactivity-provoking circumstances and manipulations.

For control, another aliquot portion of the purified starting solution was subjected to the same tests without addition of the aforesaid three reagents. Similarly to the control tests in Example 3, this solution lost most of its activity by heating at 56°C and by 1 minute of boiling at 100°C. The untreated interferon solution therefore was very labile to inactivity-provoking circumstances and manipulations.

EXAMPLE 5

To an aliquot portion of the same purified mouse interferon solution as used in Examples 1 and 2, was added a solution of dodecylamine followed by urea and liquid mercapto-ethanol. These agents were added in such amounts that the resulting solution comprised 5 M of urea, $1.4 \times 10^{-1}$M of mercaptoethanol and $2 \times 10^{-2}$M of dodecylamine.

The resulting solution was subjected to the same tests as in Example 1 and the results thereof were similar. Thus, the treated interferon solution was completely stabilised against inactivity-provoking circumstances and manipulations.

For control, another aliquot portion of the purified interferon solution was subjected to the same tests without addition of the aforesaid three reagents. Similarly to the control tests in Example 1, this solution lost most of its activity by heating at 56°C and by 1 minute of boiling at 100°C. The untreated interferon solution was, therefore, very labile to inactivity-provoking circumstances and manipulations.

What we claim is:

1. A method of stabilising interferon, comprising the following steps:
    a. providing an aqueous interferon solution comprising from about $10^1$ to about $10^6$ interferon units per milliliter and having lost substantially none of its initial activity; and
    b. treating said interferon solution with a combination of:
        i. urea or guanidine-hydrochloride as an agent for disrupting non-covalent bonds;
        ii. mercaptoethanol or ethanethiol as an agent for reducing disulfide bridges; and iii. an agent selected from the group consisting of sodium dodecylsulfate, sodium decylsulfate, sodium dodecylsulfonate, dodecylamine and decylamine as a surface-active agent; said three agents being used in such amounts that the resulting solution comprises from 0.1 to 10M of urea or guanidine-hydrochloride, at least $10^{-2}$M of mercaptoethanol or ethanethiol, and a onefold to fivefold excess of said surface-active agent calculated on the total amount of proteins in solution, respectively; so as to obtain an aqueous interferon solution which has been stabilised against activity losses.

2. The method as claimed in claim 1, wherein said aqueous interferon solution is an aqueous solution of native interferon.

3. The method as claimed in claim 1, wherein said aqueous interferon solution is a solution of purified interferon.

4. The method as claimed in claim 1, wherein said aqueous interferon solution comprises about $10^4$ interferon units per milliliter, and wherein said three agents are used in such amounts that the resulting solution comprises about 5 M of urea, from $1.4 \times 10^{-2}$M to $1.4 \times 10^{-1}$M of mercaptoethanol, and from $1 \times 10^{-3}$ to $1 \times 10^{-1}$M of surface-active agent, respectively.

5. The method as claimed in claim 1, including the further step of:
   c. removing an excess of surface-active agent and all of said other two agents by means of dialysis.

6. The method as claimed in claim 1, wherein the agent for disrupting non-covalent bonds is urea.

7. The method as claimed in claim 1, wherein the agent for reducing disulfide bridges is mercaptoethanol.

* * * * *